United States Patent [19]

Kerby

[11] Patent Number: 5,084,491
[45] Date of Patent: Jan. 28, 1992

[54] REINFORCING GLASS IONOMER DENTAL FILLING MATERIAL WITH STAINLESS STEEL, OR METALS THEREOF

[75] Inventor: Ronald E. Kerby, Columbus, Ohio
[73] Assignee: The Ohio University, Columbus, Ohio
[21] Appl. No.: 324,085
[22] Filed: Mar. 16, 1989
[51] Int. Cl.$^5$ .................................. C08L 7/00
[52] U.S. Cl. .................... 523/116; 523/115; 523/117; 524/439; 524/440
[58] Field of Search ............ 523/115, 116, 117; 524/439, 440

[56] References Cited

U.S. PATENT DOCUMENTS

| | | | |
|---|---|---|---|
| 4,209,434 | 6/1980 | Wilson et al. | 106/35 |
| 4,490,497 | 12/1984 | Evrard et al. | 523/116 |
| 4,527,979 | 11/1985 | McLean et al. | 106/35 |
| 4,738,722 | 4/1988 | Ibsen et al. | 523/116 |
| 4,797,431 | 1/1989 | Billington et al. | 523/116 |

OTHER PUBLICATIONS

John W. McLean and Oswald Gasser, "Glass-cermet cements", *Quintessence International*, vol. 16, 1985, p. 333.

D. Brown and E. C. Combe, "Effects of Stainless Steel Filters on the Properties of Polycarboxylate Cement", *J. Dent. Res.*, vol. 52, No. 2, Mar.-Apr. 1973, p. 388.

D. Brown and E. C. Combe, "Studies on Reinforced Adhesive Cements", *J. Dent. Res.*, vol. 50, May-Jun. 1971, p. 690.

"Miracle Mix", G-C Dental Industrial Corp., Tokyo, Japan.

"GC Fuji II", G-C Dental Industrial Corp., Tokyo, Japan.

*Primary Examiner*—Paul R. Michl
*Assistant Examiner*—Edward Cain
*Attorney, Agent, or Firm*—Frank H. Foster

[57] ABSTRACT

The invention relates to dental filling materials comprising stainless steel filler, a polymeric binder, and glass filler. Tensile strength, compressive strength, dentinal bonding and enamel bonding of the dental filling materials are improved relative to commercial glass ionomer cements without stainless steel.

16 Claims, No Drawings

REINFORCING GLASS IONOMER DENTAL FILLING MATERIAL WITH STAINLESS STEEL, OR METALS THEREOF

BACKGROUND OF THE INVENTION

The restoration of teeth frequently requires the placement of a core buildup filling material so as to produce adequate support prior to the construction of a crown. Teeth which have been the object of root canal treatment may additionally require the implantation of a post and/or pins prior to placement of the core buildup filling material so as to provide a suitable foundation prior to crown replacement or reconstruction.

Silicate cements have been used in the past for the repair of teeth. Silicate cement has the good properties of low thermal expansion, high abrasion resistance when not attacked by acids, and the ability to afford some caries protection by the liberation of fluoride ions.

Polycarboxylate cements are noted for their hydrophilic properties, good adhesion to tooth structure and apparent blandness. Polycarboxylate cements are based on zinc oxide, or zinc oxide and magnesium oxide or tin oxide and an aqueous solution of polyacrylic acid or an acrylic acid copolymer with other unsaturated carboxylic acids. Other additives may include silica, or alumina and bismuth salts, or stannous fluoride, or tannic acid. In the setting reaction, zinc polyacrylate is formed together with other metal polycarboxylates. These materials, however, have insufficient strength to be used as a core material.

The two most widely used and clinically effective core buildup filling materials are silver amalgam and composite resins. Silver amalgam exhibits high strength, usually in the range of from 300 to 400 MPa (megapascals). Both silver amalgam and composite resins possess coefficients of thermal expansion which are two to three times that of tooth material. This is a significant disadvantage and may result in increased microleakage and may lead to recurrent caries and/or solubility of the post luting cement. Other disadvantages of the silver amalgam and the composite resins include possible corrosion of the amalgam at the post and core material interface and lower compressive strength of the composite resin. Composite resin and amalgam also frequently require the placement of pins in conjunction with a post in order to obtain adequate retention of the core buildup material. Furthermore, both materials lack the ability to provide desirable chemical bonding to dentin, which may further increase the propensity for microleakage.

Glass ionomer cement filling materials have been previously developed which have addressed some of the above disadvantages of amalgam and composite resin. Glass ionomer cement has strength characteristics similar to those cited above for silicate cement but is more resistant to acid attack. It is also bland, like the polycarboxylate cements, but with the added advantage of translucency.

Glass ionomer cements utilize the hardening reaction between ion-leachable glasses and aqueous solutions of a polymeric binder such a homo- and copolymers of acrylic acid and/or itaconic acid. When the glass and the binder are mixed, $H^+$ ions from the acid of the liquid penetrate the surface layers of the glass particles. Cations including $Al^{+3}$ and $Ca^{+2}$ are displaced and the aluminosilicate network of the glass surface is degraded to a hydrated siliceous gel. Cations, either simple or as fluoride complexes, migrate into the aqueous phase of the cement paste where metallic salt bridges are formed between the long chains of charged polycarboxylate ions, crosslinking them and causing the aqueous phase to gel and the cement to set. Calcium ions are more rapidly bound to the anion of the polymeric binder than are aluminium ions and it is the calcium ions which are responsible for the initial set. Subsequent formation of the aluminum salt bridges accounts for the hardening of the cement. Thus a dual setting reaction exists for glass ionomer cements consisting of a calcium ion-exchange (initial setting) and an aluminium ion-exchange (final hardening setting). Adhesion between the glass ionomer adhesive and a tooth substrate results from the dipole and ionic interactions because glass ionomer cements and the substrates having a polar nature.

The glass ionomer cements generally consist of, for example, a polycarboxylic acid material and glass, such as finely ground aluminosilicate glass. Such glass ionomer cements will adhere to the dentin of the tooth without the need for a bonding agent or primer or coupling agent. In addition, these cements are able to provide a source of desirable flouride ion leachable from the glass. Flouride ion has been shown to be an effective agent in the prevention of caries. Also, glass ionomer cements are generally biocompatible with the dental tooth pulp. However, some glass ionomer cements are sensitive to water as evidenced by a reduction in adhesion and/or compressive strength over time upon exposure to moisture. Furthermore, the tensile strengths in general of unreinforced glass ionomer cements are not sufficient. These disadvantages make the unreinforced glass ionomer cements unsuitable as core buildup materials.

It is known to improve the tensile and/or compressive strengths of the glass ionomer cements used as a core buildup material by the addition of certain metallic fillers, such as silver, or silver alloy powders, such as dental amalgam. This results in certain improved properties which make the reinforced cement useful as a core buildup material for the restoration of teeth prior to crown replacement. These properties include: (1) a coefficient of thermal expansion similar to that of tooth structure; (2) increased strength when compared to conventional unreinforced glass ionomer cements; and (3) the release of fluoride ions to adjacent teeth. Commercially available silver reinforced glass ionomer cements have compressive strengths of approximately 168 to 175 MPa. The addition of silver or silver alloys to the glass ionomer cement produces increased strength when compared to unreinforced glass ionomer cements.

It has been shown, however, that simple mixtures of metal powders and aluminosilicate glass ionomer powders often fail to provide any metal/polyacrylate bond, which subsequently can lead to increased wear of the filling material.

McLean and Gasser have recommended the use of a sintered cermet glass/metal composition to increase the bond strength between the glass and various metal fillers and to decrease abrasion resistance. In glass-cermet cements, the glass and metal powders are sintered or fused to high density, ground, and the powdered mixture then combined with acids to form the final cements. Several of the precious metals well-known in dentistry may be used in the preparation of glass-cermet cements, but gold and silver are the most suitable. Cermet cements differ from simple mixtures of metal and glass powders since the metal powder is firmly bonded to the glass by high temperature sintering.

McLean et al., Quintessence International, volume 16, page 333, (1985), teach the use in cermet cements of various metals including alloys of silver and tin, pure silver, gold, titanium, and palladium. Gold and silver were disclosed as metals which form suitable cermets with the aluminosilicate glass. However, the compressive and/or tensile strength of these metal-reinforced glass ionomer cements was still inadequate for high stress tooth areas.

Brown and Combe (J. Dent. Res. March-April 1973, vol. 52 No. 2, page 388) have reported the use of stainless steel in polycarboxylate cement. The stainless steel was chosen therein for its supposed ability to form an adhesive bond with this type of cement. This study did not use glass ionomer cements which employ significantly different chemistry than is employed in polycarboxylate cements. Furthermore, the Brown and Combe study relied, for the setting of the cement, on the presence of zinc ions from the zinc oxide used in polycarboxylate cements.

Brown and Combe (J. Dent. Res., vol. 50 page 690, 1971), reported the investigation of stainless steel as a potential reinforcing agent for zinc polycarboxylate cements. The study did not use glass ionomer cements, but instead used zinc oxide and polycarboxylate. The study concluded "that polycarboxylates are too brittle to be improved substantially by metallic fillers in accordance with the theory of reinforcement".

Therefore, a need exists for an improved metal-reinforced glass ionomer dental material which produces a more economical, very strong, fracture resistant dental core filling material. The metal reinforced cement should be applicable in all situations in which the commercially available cements are utilized, including among others: (1) core buildup filling material prior to crown preparation; (2) core filling material in combination with a prefabricated post to restore root canal treated teeth; (3) temporary or permanent filling material of primary or permanent teeth or dental implants, and (4) a luting agent for the cementation of permanent dental restoratons.

SUMMARY OF THE INVENTION

It is an object of the present invention to provide a dental filling material, comprising a polymeric binder, glass, and stainless steel filler, which overcomes the above disadvantages.

Another object of the present invention relates to a dental filling material comprising a glass filler, a polymeric binder, and a base metal filler, wherein the base metal is any base metal filler or non-precious metal which can ionize to produce a positively charged metal ion and which can react with and be bonded by the polymeric binder. The base metal filler useful in this embodiment can thus be any metal, or combination of metals, or oxides thereof including iron, chromium, nickel, carbon, titanium, manganese, tin, molybdenum, silicon, indium, or alloys or mixtures thereof. Thus galvanized steel, ferritic steel, austinitic steel and martenistic steel are also operative herein within the meaning of metal filler. Any modifications of the above materials by reacting with, or making an alloy with, or mixing with, or treating with aluminum, zinc, or titanium are also operative herein as metal fillers.

The present invention also relates to a dental filling material comprising stainless steel and a composite resin. The stainless steel can be combined with a dental composite resin in the absence of glass powder whereby curable dental filling materials are produced.

Another object of the present invention relates to a method of preparing a dental cement comprising a polymeric binder, glass and stainless steel filler.

Yet another object of the present invention is a method of repairing or restoring primary or permanent teeth.

A further object of the present invention is a method for cementing crowns to teeth or dental posts to the root canal of a tooth.

Another object of the present invention is a method of cementing crowns to teeth or dental implants or dental posts into the root canal of the tooth.

DETAILED DESCRIPTION OF THE INVENTION

It has been surprisingly discovered that dental filling materials of superior compressive and tensile strengths can be produced by the addition of stainless steel filler to glass ionomer cements. Use of stainless steel powder in glass ionomer cements for dental filling materials is heretofore unknown to the inventor.

By "dental filling material" herein is meant dental cements, silver amalgams, composite resins, glass ionomer cements, unfilled resins, and the like, useful in filling, repairing, or reconstruction of teeth or the preparation of crowns for teeth. Luting cements, filling cements, lining cements, dental adhesives, core buildup materials, and the like are also included within the meaning of "dental filling material" herein.

In one embodiment of the present invention, stainless steel filler is combined with an organic polymeric binder and glass to produce a dental filling material. More specifically, stainless steel powder is mixed or blended with an acidic polymeric binder and glass powder.

In one embodiment of the present invention, the polymeric binder is an acidic organic monomer or polymer. The acidity of the organic monomer or polymer is not a limitation of the present invention but an acidic polymeric binder is preferred herein because of the acid leaching utilized to promote cure of glass ionomer cements, as described supra. Thus, the proton of, for example, a hydroxyl group on a hydroxyl-functional polymer may be sufficiently acidic to produce an acceptable polymeric binder in some applications. A preferred polymeric binder material herein is a carboxy-functional organic material. By "carboxy-functional" herein is meant a carboxylate anion-containing material where the carboxylate group can be COOH or COOR, where R can an alkyl group, an alkenyl group, an alkynyl group, an aralkyl group, an alkaryl group, an aryl group, or a precursor to or derivative of any such group, or any other chemical group capable of producing a $COO^-$ anion.

By "polymeric binder" herein is meant a curable organic material selected from the group consisting of organic monomers, organic polymers, organic ionomers, organic copolymers, organic terpolymers, and mixtures thereof. Glass ionomer cements are also included within the meaning of "polymeric binder" herein.

By "curable" herein is meant the ability to chemically or photochemically crosslink, polyermize, or otherwise advance in molecular weight to such a degree as to become a hard, essentially insoluble in water, polymeric material or resin or combination thereof. The cure can be induced by, if necessary, cure enhancers, cure accelerators, catalysts, curing agents, crosslinking agents, and the like. Cure enhancers can include, but are not limited to, for example, organic acids, inorganic acids, benzoyl peroxide, camphoroquinone, and amines. If a photocurable polymeric binder is used alone or in conjunction with other binders, a photoinitiator may also be added.

The curable organic material useful as a polymeric binder in the present invention is preferably selected from the group consisting of organic acids, polyesters, phenol-formaldehyde resins, polyimides, polyamides, polycarbonates, polycarboxylic acids, epoxy resins, polyacrylate resins, composite resins, polyurethane resins, silicone resins, polymethylacrylate resins, aromatic dimethacrylate resins, urethane diacrylate resins, polymethylmethacrylate resins, and mixtures or derivatives thereof. A more preferred curable organic material useful herein as a polymeric binder is a polycarboxylic acid, such as, for example, itaconic acid, tartaric acid, acrylic acid or polyacrylic acid, and maleic acid or polymaleic acid, or polymers and/or copolymers or mixtures thereof. Halogenated derivatives of the aforementioned acids are also useful herein as a comonomer. Thus in one embodiment, the polycarboxylic acid is prepared by the homo-polymerization or co-polymerization of unsaturated aliphatic carboxylic acids, for example acrylic acid, 2-chloroacrylic acid, 3-chloroacrylic acid, 2-bromoacrylic acid, 3-bromoacrylic acid, methacrylic acid, itaconic acid, citraconic acid, and fumaric acid. Suitable monomers for co-polmerizing with the unsaturated aliphatic carboxylic acids include unsaturated aliphatic compounds such as for example acrylamide, acrylonitrile, vinyl chloride, allyl chloride, vinyl acetate, and 2-hydroxyethyl methacrylate.

The binder can also be a photocurable resin such as, but not limited to, olefinic resins. The binder can also be a composite resin capable of homopolymerization.

The binder can also comprise a polymerizable Bis-GMA resin. Bis-GMA is 2,2-bis[4(2-hydroxy-3-methacryloloxypropyl-oxy)-phenyl]-propane. The Bis-GMA resin can be polymerized by an organic amine accelerator or a photoinitiator, such as, for example, a diketone. Bis-GMA can be used in the present invention in conjunction with a glass ionomer cement.

The acidic polymeric binders useful in the present invention can be liquid, solid, semisolid, or paste at ambient conditions. When used as a solid in the present invention, the acidic polymeric material can be dehydrated, freeze dried, or spray dried liquid material. Thus in one embodiment of the present invention, stainless steel powder, glass powder and polymeric binder powder are combined, to be activated later for cure upon the subsequent addition of water or water and acid.

The glass, also referred to herein as glass filler, useful in the present invention can include silica, silicate glass, fluorosilicate glass, fluoroborosilicate glass, calcium silicate glass, calcium alumino silicate glass, aluminosilicate glass, calcium aluminum fluorosilicate glass, and the like, or mixtures thereof, or any other ion-leachable glass, ceramic material, or porcelain material. The glass used in the present invention can also be glass ionomer powder. The preferred glasses are aluminosilicate glass, calcium aluminum fluorosilicate glass, and fluorosilicate glass. The particle size of the glass useful in the present invention is less than 150 microns, preferably in the range of from 0.01 micron to 120 microns, and more preferably in the range of from about 20 microns to about 100 microns. The glass can be ground particles, powder, amorphous, crystalline, or spheroidal in shape.

The stainless steel useful herein as a metal filler in glass ionomer cements can be, but is not limited to, any of the conventional stainless steel materials. Also useful herein is Elgiloy which is a cobalt-chromium alloy which also contains iron. Stainless steel can vary in its composition, but commonly possesses some or all of the following: iron, chromium, nickel, carbon, titanium, manganese, and molybdenum. These materials can be present in the stainless steel useful herein in any amounts. Additionally, the stainless steel useful herein may be contacted with tin, indium, zinc, and/or aluminum.

There is no known limitation as to the smallest particle size of the stainless steel particles useful in the dental filling material of the present invention. It is preferred that the particles be small enough that the polymeric binder can wet and surround the particles to an extent sufficient to bind the particles strongly together once the polymer binder cures. It is further desired that the particles be small enough that they can be easily worked into the surface irregularities of teeth under repair or reconstruction. In one embodiment of the present invention, the stainless steel filler is of particle size ranging from about 0.01 micron to about 150 microns, although particles less than 0.01 micron in size are also operative herein. In a more preferred embodiment, the filler particles are of a size ranging from about 5 microns to about 45 microns. Stainless steel filler in the powder form or fine fiber form is preferred in the dental cements of the present invention.

The stainless steel useful herein can be sintered with other metals or metal alloys or with glasses or glass ionomer powders or porcelain materials or ceramic materials. The stainless steel filler can also be coated with any chemicals, or composite resins, or glass ionomer cements. Any modifications of the above materials by reacting with, or making an alloy with, or mixing with, or treating with aluminum, zinc, or titanium are also operative herein as stainless steel fillers.

In luting cements (Type I) used to hold dental crowns to the post, core, or tooth structure being repaired, the ideal filler is generally less than or equal to about 25 microns because this is generally the minimum gap space achievable between the crown and the tooth. Thus the filler particles must be smaller than the gap space so as to fit within the gap along with sufficient polymeric binder to achieve adhesion. Therefore, when the dental filling materials of the present invention are to be used in luting cements, or for cementing crowns to teeth or dental implants, or for cementing posts to root canals of a tooth, the desirable stainless steel particle size is less than or equal to 25 microns. Luting cements are generally of lower viscosity than filling cements (Type II) because luting cements contain generally more liquid phase, whereas filling cements are more highly filled systems. Filling cements generally use a higher powder to liquid ratio than luting cements use and the filler particles in filling cements can be more than 25 microns in size. Thus when the dental cements of the present invention are to be used as filling cements, the stainless steel particles can be up to about 150 microns in size, but more preferably are 10 to 45 microns. Smaller filler particle size produces greater surface area which results in better wetting of the polymeric binder onto the filler, increased surface area for bonding, and improves the set time of the binder. The compressive and tensile strengths of the cured dental filler materials of the present invention may also improve with smaller stainless steel particle size.

The stainless steel used as a filler in the dental filling materials of the present invention has chromium, iron and other positively charged ions, or oxides thereof, on its surface. It is believed that these cations bind to the carboxylate anion in the polymeric binder, such as a glass ionomer cement, better than metal ions of the prior art dental amalgams bind to the carboxylate anion. It is also believed that iron, chromium, and/or any other positively charged ions, or oxides thereof, on the surface of the stainless steel may be replacing at least some of the aluminum ions from the glass which, as described above, replace some or all of the calcium ions leached from the glass in the final setting of the dental cement or form metal-ion bridges. It is believed by the inventor, who does not wish to be limited to the theory, that the replacement of a certain fraction of the aluminum ions responsible for the final hardening of the cement with iron, chromium, and/or other positively charged ions from the stainless steel filler may account for the increased bonding or significant improvement in the physical properties of the hardened dental filling materials of the present invention.

In a more preferred embodiment of the present invention, the stainless steel particles used in the dental filling material are at least essentially spheroidal. It is believed that the spheroidal shape of the particles reduces the propensity for crack propagation in the cured cement as well as enhancing the bonding between the ions of the stainless steel surface and the acidic polymeric binder. Furthermore, the spheroidal particles are surprisingly more easily manipulated than are fibers and are more easily wet by the polymeric binder. It is further believed that the preferred spheroidal nature of the stainless steel particles provides the greatest possible density of close packing in the dental filling material which thereby improves the compressive and tensile strengths. Thus while stainless steel fibers up to about 2 millimeters in length and up to 100 microns in diameter are operative herein, spheroidal stainless steel particles are preferred.

The amount of stainless steel powder utilized in the dental filling material of the present invention is limited only by the ability of the polymeric binder to mix with the stainless steel to form a dental filling material mixture which, prior to cure of the polymeric binder, exhibits a workable viscosity, a useful working time, and adequate set strength. The "working time" is the time before cure of the polymeric binder during which the dental filling material of the present invention remains soft and workable. It is during the working time that the dentist applies the dental filling material to the prepared tooth surface and/or post, core, and tooth surface, and/or tooth surface and pins, or into root canals to form any other restoration prior to application of a crown. Working time may be reduced as the stainless steel particle size is reduced because of the increase in surface area. Working time may be substantially increased by mixing the material on a cold slab and/or by refrigerating one or more of the components. It is desirable for the dental filling material of the present invention prior to cure of the polymeric binder to exhibit a working time before cure of the polymeric binder of approximately 30 seconds to 10 minutes.

A workable consistency of the polymeric binder/stainless steel/glass filler mixture prior to cure of the binder is desirable but the exact viscosity can vary according to the desires of the dentist and the requirements of the specific restoration. The viscosity of the dental filling materials of the present invention can vary with the practicing dentist and are not limitations of the present invention. Low viscosities are desirable when the dental filling materials of the present invention are used as luting or lining cements. For core buildup, it is desirable to add the powder or powders to the liquid binder until the heaviest workable viscosity of the mix is obtained, prior to the mix losing its sheen. A sheen is generally indicative of residual free organic binder available for bonding. A sheen also demonstrates that the cure of the material has not yet advanced to an undesirable working viscosity. When the polymeric binder is present in solution, an increase in either molecular weight or concentration will increase the viscosity of the binder, but may adversely effect the working properties of the material. Viscosity increases of the polymeric binder also occur due to hydrogen bonding between separate molecular chains of the polymeric binder. This problem is significantly reduced by using dry forms of polymeric binder, such as dehydrated, freeze dried, or spray dried polycarboxylic acid. Using dry forms of the polymeric binder also increases the shelf life of the dental filling materials. The liquid for cement formation can then be either water or an aqueous solution of an acid, such as tartaric acid and/or itaconic acid. The viscosity of the dental filling material prior to cure of the binder can be designed by varying (1) the ratio of polymeric binder to stainless steel powder, (2) the particle size distribution of the stainless steel powder, (3) the particle size of the glass ionomer powder, (4) the temperature of one or more of the components, (5) the molecular weight of the polymeric binder, (6) the liquid to powder ratio, (7) the effective concentration of the polycarboxylic acid in solution, and/or (8) the use of solid or liquid diluents, modifiers or enhancers in the acidic polymeric binder.

The weight ratio of stainless steel powder to glass filler can vary according to the present invention from about 5:1 to about 1:100, but a preferred weight ratio is, for example, from about 1:4 to about 1:1. This ratio can be varied by the skilled artisan depending upon the particle size distribution and composition of the stainless steel filler and the physical properties of the glass filler. A preferred volume ratio of stainless steel filler to glass filler is approximately 10% to 19% stainless steel.

In a preferred embodiment of the present invention, the dental filling material has weight ratios of components in the dental filling cement ranging from about 10% to about 95% glass filler, wherein the glass filler is of a size ranging from about 1 micron to about 200 microns, 1% to about 80% stainless steel filler, of particle size ranging from about 1 micron to about 45 microns, and from about 1% up to about 75% polymeric binder.

It is desirable according to one embodiment of the present invention to achieve a rapid initial partial cure of the dental filling material to a degree sufficient to produce a self supporting dental structure, followed by a full and complete cure during which adequate strength and adhesion are achieved. This initial partial cure can be achieved, for example, self-curing or homopolymerization techniques or by the addition to the dental filling material of a photocurable resin in conjunction with a photoinitiator. The photocurable resin can be cured by conditions and techniques known to those skilled in the art.

Dental filling cements of the present invention possess significantly higher tensile strengths and compressive strengths than the strengths of commercially available silver reinforced glass ionomer cements. Thus by the present invention a compressive strength 268 MPa is achieved compared to 168 to 175 MPa for commercial metal reinforced glass ionomer cements. (See Table I) By the present invention, a diametral tensile strength of about 23 MPa is achieved within 24 hours after setting of the cement, whereas commercial cements displayed diametral strength of 10 to 14 MPa. Therefore, the inventive stainless steel reinforced glass ionomer cement is more than 50% stronger than either of the commercially available cements without stainless steel.

In addition, the stainless steel reinforced glass ionomer cement of the present invention exhibits significantly improved dentinal and enamel bonding, relative to commercially available cements. (See Table III) The stainless steel reinforced glass ionomer cement of the present invention exhibited dentinal and enamel bond strengths which were 30% to 146% higher than the bond strengths of the two commercially available glass ionomer cements. The inventor believes, but does not wish to be limited to the theory, that improved strengths are attained because (1) the stainless steel particle is able to achieve stronger adhesion to the polymeric binder than other metals in the conventional metal reinforced glass cements, and/or (2) the formation of stronger iron or chromium ion bridges within the polymeric binder/glass ionomer matrix. Increased bonding may result from strong metal ion bridges between iron and chromium and the collagen or calcium hydroxyapatite in the tooth structure.

Thus the present invention relates to a method of preparing a dental filling material comprising: combining stainless steel powder of particle size ranging from about 0.01 micron to about 150 microns, glass filler, and an acidic polymeric binder selected from the group consisting of curable organic polymeric materials, whereby a dental filling material is obtained. Alternatively, the glass filler can be a glass ionomer cement powder. The glass and the binder components can be either mixed together before adding the stainless steel particles, or at the same time the stainless steel is added to polymeric binder.

Furthermore, the order of mixing of the components of the dental filling materials of the present invention is not a limitation herein. Thus the stainless steel particles can be mixed with the polymeric binder or with the glass particles. In this manner, dental filling material precursors can be prepared wherein any two of the three components can be combined in one part and the third component packaged separately in the second part. Any two or three of the components can be packaged separately. Thus two part and three dental filling systems are herein provided utilizing stainless steel fillers. Four part systems can be produced by using water or water and acid as the fourth part. The order of addition can also be varied depending on the use of solid, paste, semisolid, or liquid polymeric binder materials.

The dental filling material of the present invention can further comprise one or more additives selected from the group consisting of cure enhancers, crosslinking agents, pigments, radiopaque materials, primer materials or coatings, tooth surface conditioners, adhesion promoters, synthetic enamel, oxidation inhibitors, photocurable resins, tooth surface conditioners such as tannic acid, or ferric chloride, or dodicin, photoinitiators, and the like. These additives can include, for example, amines such as ethanolamine, triethanolamine, sodium tripolyphosphate, titanium dioxide pigment, calcium hydroxyapatite, camphoroquinone, diketones, and benzoyl peroxide. Tooth surface modifiers such as mineralizing agents well known the the skilled artisan are also useful additives herein.

The dental filling material of the present invention can further comprise precious metals, non-precious metals, silver, silver alloys, silver-tin alloys, gold, gold alloys, tin, indium, aluminum, zinc, manganese, copper, and the like.

It is believed, but the inventor does not wish to be limited to the theory that, the treatment of stainless steel powder or filler with acid prior to mixing the stainless steel with the glass filler and then the polymeric binder according to the present invention, increases the ionization of the surface of the stainless steel such that additional iron, chromium, and/or other positively charged ions, or oxides thereof, are available for forming metal ion bridges with the polymeric binder matrix or displacing aluminum ions in the hardening step of the setting process.

Thus the present invention also relates to a method of preparing a dental filling material further comprising prior to combining the stainless steel powder, the glass filler, and the polymeric binder, the step of treating the stainless steel powder of spheroidal particle size ranging from about 0.01 microns to about 45 microns with an acid. The acid treated stainless steel can then be combined directly with the polymeric binder or the glass or both. The combining of the components can be mechanical mixing or trituration. Alternatively, the acid treated stainless steel can be filtered or seived to separate the stainless steel powder from the acid and then washed with water or alcohol or both. The acid used to treat the stainless steel powder can be, for example, selected from the group consisting of hydrochloric acid, sulfuric acid, phosphoric acid, acetic acid, propionic acid, perchloric acid, hydrofluoric acid, and nitric acid, or aqueous solutions thereof. Other organic and inorganic acids are also operative herein for treating the stainless steel for activating or ionizing the surface. The concentration of the acid used to treat the stainless steel is not a limitation herein, but can range from about 1% to about 100%, but a more preferred concentration is from about 5% to about 25%. Other conventional metal cleaning steps effective for removing grease, oil, dirt, or other organic or inorganic materials present on the surface of the stainless steel are also contemplated herein for preparing or activating the stainless steel. Thus solvent washing of the stainless steel, for example, is also contemplated herein as an effective way to activate the stainless steel particles.

Any known method for cleaning and/or activating the surface of metals is useful, but may not be required, herein for the preparation of the stainless steel filler for use in the dental filling materials.

The present invention also relates to a method of repairing primary or permanent teeth or dental implants or cementing a crown to a tooth, comprising: a) combining stainless steel powder of spheroidal particle size ranging from about 0.01 microns to about 45 microns with an acidic or carboxy-functional polymeric binder selected from the group consisting of organic acids, polyesters, polyamides, polyimides, polycarbonates, epoxy resins, polyurethane resins, silicone resins, polycarboxylic acids, polyacrylate resins, polymethylacrylate resins, and polymethylmethacrylate resins, and mixtures or copolymers thereof, with a glass filler in a weight ratio of stainless steel to glass filler of from 5:1 to 1:100, and wherein the glass filler is present in a total percentage by weight of from about 10% to about 95%, whereby a dental filling material is obtained; b) applying the dental filling material from step a) to a surface of a primary or a permanent tooth and/or a dental implant or a dental posts and/or pins or a crown in an amount and in a configuration sufficient to effect the desired repair or cementation; and c) allowing the binder of the dental filling material to cure, set, or otherwise harden, polymerize, crosslink or react. The stainless steel used in the method to repair teeth can be treated with an acid or, it is believed, high temperature in the presence of oxygen, prior to mixing with the polymeric binder and glass to thereby improve the adhesion and strength of the dental filling material. Other surface treatments known or obvious to those skilled in the art effective for increasing the surface bonding of the polymeric binders to the stainless steel are within the scope, spirit, and intent of the invention.

The present invention further relates to a dental filling material comprising stainless steel filler and a composite resin. The stainless steel filler can be combined with a composite resin in the absence of glass powder or a glass ionomer cement to produce curable dental filling materials. Stainless steel has not been heretofore known as a metal reinforcer for use with dental composite resins.

It is believed that all the above embodiments of the present invention utilizing stainless steel as a filler for glass ionomer cements can be modified by the addition to or the replacement of the stainless steel filler with any base metal including, but not limited to, chromium, iron, nickel, carbon, silicon, indium, molybdenum, manganese, titanium, tin, copper, zinc or oxides thereof and other non-precious, preferably non-sintered metals, or precious metals, or mixtures thereof. These are metals commonly found in stainless steel and are also operative herein in a form or forms other than stainless steel. Thus singularly or in mixtures of at least any two, the aforementioned base metals can be combined with a polymeric binder or composite resin and glass powder to produce useful dental filling materials. Any modifications of the above materials by reacting with, or making an alloy with, or mixing with, or treating with aluminum, zinc, or titanium are also operative herein as base metal fillers. In the dental filling material of the present invention, the stainless steel powder filler can also comprise particles of base metal which have been stainless steel or chromium coated or plated.

The base metals can be in powder form, crystalline form, amorphous, or as fibers. The preferred size of the base metal particles useful in this embodiment as metal fillers is from about 0.01 microns to about 150 microns, and more preferably from about 5 microns to about 45 microns It is believed that the base metals particles will have sufficient positive ions on their surfaces to facilitate bonding between the polymeric binders used herein, and the glass particles used herein. Any metal which can ionize to produce a positively charged metal ion is expected to react with and be bonded by the organic polymeric binders useful herein. Thus the present invention also relates to a dental filling material comprising an acidic polymeric binder, glass filler, and a filler comprising a sintered or non-sintered metallic material selected from the group consisting of any base metal, including but not limited to chromium, iron, nickel, tin, titanium, carbon, manganese, molybdenum, silicon, and oxides thereof, and sintered or non-sintered mixtures thereof.

Thus another embodiment of the present invention utilizes galvanized steel filler, or ferritic steel filler, or austinitic steel filler, or martenistic steel filler with a polymeric binder and glass powder or with a composite resin. Thus, for example, Elgiloy brand alloy, which is approximately 20% chromium and 15% iron, among other metals, will, as a metal reinforcer for glass ionomer cements, provide significant strength improvement compared to commercially available silver-reinforced glass ionomer cements.

The following examples are provided as illustrations of the present invention and are not to be viewed as limitations thereof.

EXAMPLE 1

Acid Treatment of Stainless Steel Powder

Stainless steel powder (316 L) of particle size less than or equal to about 25 microns was stirred in a 5% aqueous solution of hydrochloric acid at about 23 degrees Centigrade for three minutes, filtered, and then washed with distilled water and then with anhydrous methanol. The stainless steel was then filtered from the solution and dried in a vacuum oven to produce clean, grease-free particles.

EXAMPLE 2

Stainless Steel Glass Ionomer Cement Powder

The acid-treated stainless steel powder of Example 1 was mixed with a Type II glass ionomer cement powder commercially available as "GC Fuji II Glass ionomer for restorative filling", obtained from G-C Dental Industrial Corporation, Tokoyo, Japan, distributed by G-C International Corporation, of Scottsdale, Ariz. The materials were mixed at a stainless steel powder to glass ionomer powder ratio of 8.22 grams to 15 grams, respectively. The resulting combination was then mechanically tumbled in a closed container and then filtered through a 325 mesh (45 micron) screen until the stainless steel powder was evenly dispersed in the glass ionomer cement powder.

EXAMPLE 3

Stainless Steel Glass Ionomer Cement (SS/GI)

The uniformly dispersed mixture of stainless steel powder and glass ionomer powder from Example 2 was then mixed with the liquid polyacrylic binder portion of "GC Fuji II Glass ionomer" at a ratio of 2.0 grams of powder to 0.39 grams of liquid polyacrylic binder. The materials were mixed on a clean glass cement mixing slab with hand spatulation at room temperature (23 degrees Centigrade) until all powder and liquid were incorporated, whereby a stainless steel reinforced glass ionomer cement was obtained. Mixing time of 35 seconds or less was maintained through the use of a stop clock.

EXAMPLE 4

Physical Properties

Cylindrical specimens 6 mm × 12 mm of the mixed cement of Example 3 were prepared in siliconelubricated stainless steel split molds and maintained in distilled water at 37 degrees Centigrade for 1 hour and 24 hours, and then the cured specimens were randomly tested on an MTS machine with a crosshead speed of 0.5 mm/min. (dimetral tensile) and 1.0 mm/min. (compressive). The stainless steel reinforced glass ionomer cement of Example 3 was evaluated for percent solubility in 0.01 M lactic acid over 24 hours (% Sol), working time (W.T.) and setting time (S.T.).

Table I illustrates the results of the comparison of tensile and compressive strengths after 1 hour and 24 hour set times for stainless steel reinforced glass ionomer (SS/GI) to properties of two commercially available silver-reinforced glass ionomer cements, known as Ketac-Silver (KS), which is available from ESPE Dental Products, West Germany, and Fuji II Miracle Mix (MM), available from GC International, Scottsdale, Ariz. MM is a mixture of a silver amalgam alloy powder and Type II glass ionomer cement. Ketac-Silver is a cermet silver reinforced glass ionomer cement in which aluminosilicate glass is fused into fine silver particles.

TABLE I

| Cement | Mean Tensile (MPa) | | Mean Compressive (MPa) | |
|---|---|---|---|---|
| | 1 hr | 24 hr | 1 hr | 24 hr |
| SS/GI | 18.2 | 22.7 | 164.1 | 268.3 |
| KS | 12.7 | 14.2 | 117.2 | 175.3 |
| MM | 10.3 | 10.9 | 102.7 | 168.7 |

SS/GI = Stainless Steel Reinforced Glass Ionomer Cement
KS = Ketac-Silver
MM = Miracle Mixture Table II illustrates the results of the comparison of working time (W.T.), setting time (S.T.), and percent solubility in 0.01M lactic acid over 24 hours of the two commercially available silver-reinforced glass ionomer cements identified above and the stainless steel reinforced glass ionomer cement of the present invention.

TABLE II

| Cement | W.T. | S.T. | % Sol |
|---|---|---|---|
| SS/GI | 3:00 | 3:40 | 1.95 |
| KS | 3:10 | 4:10 | 1.67 |
| MM | 2:10 | 3:20 | 2.51 |

% Sol = percent solubility in 0.01 M lactic acid over 24 hours
W.T. = working time in minutes
S.T. = setting time in minutes
SS/GI = Stainless Steel Reinforced Glass Ionomer Cement
KS = Ketac-Silver
MM = Miracle Mixture The results illustrated in Tables I and II show the inventive stainless steel reinforced glass ionomer cement to be more than 50% stronger than either of the commercially available cements without stainless steel filler. ANOVA and Tukey's Studentized Multiple Range Test indicated significant differences between the inventive and the commercially available cements for both compressive and tensile strengths at 1 hour and 24 hours ($P < 0.0001$).

EXAMPLE 5

Shear Testing

The shear bond strength to enamel and dentin of the stainless steel reinforced glass ionomer cement (SS/GI) of Example 3 was compared with one conventional glass ionomer cement (Fuji II glass ionomer restorative) shown in Table III as "G", and two commercially available silver reinforced glass ionomer cements (Fuji II Miracle Mix, and Ketac-Silver), shown in Table III as MM and KS.

Eighty freshly extracted noncarious human molar third teeth were hand debrided, pumiced, and stored in closed bottles containing distilled water at 23 degrees Centigrade. Teeth were then randomly divided into two groups of forty teeth each. One group of specimens was prepared for dentinal bonding and the other for enamel bonding.

Teeth prepared for dentinal bonding were sectioned horizontally at the contact area with a circular diamond saw on a macrotome slicing machine to remove the occlusal portion of the clinical crown in order to expose the outer layer of occlusal dentin. Root resection and the placement of retentive undercuts were performed prior to embedding. The occlusal surfaces of the extracted teeth were then pressed into boxing wax and mounted occlusal face down in a 30 mm diameter by 12 mm high plastic ring mold with slow-setting epoxy resin. After removal from the mold and boxing wax, the exposed occlusal dentin was sequentially fine sanded with 240 to 600 grit silicon carbide paper and water to produce a flat smooth dentinal surface.

Teeth prepared for enamel bonding were similarly mounted in epoxy resin so that the buccal surface was exposed after removal from the plastic ring mold. The exposed buccal enamel was also fine sanded with 240 to 600 grit silicon carbide paper and water to produce a flat enamel surface. All specimens were maintained in distilled water at 37 plus or minus 2 degrees Centigrade until bonding.

Four glass ionomer cements were tested: two commercially available silver reinforced cements (MM and KS), one conventional glass ionomer cement (G), and the inventive stainless steel reinforced glass ionomer cement of Example 3 (SS/GI). For the commercially available cements, the manufacturer's specifications as to proper mixing time and powder-to-liquid ratio were carefully followed. Spatulation was performed on a glass cement slab at room temperature until all powder and liquid were incorporated. Mixing time of 35 seconds or less was maintained by the use of a stop clock. Prior to bonding, tooth surfaces were passively conditioned with 40 % polyacrylic acid (obtained from Durelon Liquid, ESPE Premier) for 10 seconds, rinsed with distilled water for 10 seconds and dried with warm air using a hair dryer to prevent oil contamination. After surface preparation, a small stainless steel cylinder 4.2 mm O.D. × 4.0 mm I.D. × 3.0 mm high was centered on the exposed tooth surface. A fresh mix of cement was condensed inside the cylinder against an area of tooth surface 4 mm in diameter. The area of bonding was approximately 12.6 sq.mm. The bonded specimens were then allowed to set in air at 23 degrees Centigrade and 50% RH for 10 minutes from the start of mix. After completion of set, the exposed area at cement was coated with a protective varnish (obtained from Espe Premier). All bonded specimens were maintained at 37 degrees Centigrade and 100% RH for a period of 7 days during which time they were subjected to thermocycling in water baths at 10 degrees and 50 degrees for 1 minute dwell time per bath and 1500 cycles.

Ten bonded specimens of each cement type were tested for both dentinal and enamel bond strength. At the time of testing, each bonded specimen was tightly inserted in a custom made stainless steel jig. The specimens were randomly tested in shear mode at a cross head speed of 0.5 mm/minute on an MTS testing machine utilizing a stainless steel plunger head and the minimum load required to induce bond failure was recorded.

The results of the shear test are shown in Table III.

TABLE III

| Mean Bond Strength To Dentin And Enamel (MPa) | | |
|---|---|---|
| Cement | Enamel | Dentin |
| SS/GI | 13.1 | 10.1 |
| MM | 9.9 | 7.7 |
| G | 9.3 | 5.3 |
| KS | 7.1 | 4.1 |

ANOVA and Tukey's Studentized Multiple Range Test indicated significant differences between the inventive stainless steel glass ionomer cement and commercially available metal reinforced cements for both enamel and dentinal bonding ($P < 0.0001$) The stainless steel reinforced glass ionomer cement exhibited dentinal and enamel bond strengths which were 30% higher than the bond strengths of Miracle Mix and 146% and 85% higher than those of Ketac-Silver.

I claim:

1. A method of preparing a dental filling material comprising
   (a) treating stainless steel powder of spheroidal particle size ranging from about 5 microns to about 45 microns with an acid, or aqueous solution thereof; and
   (b) combining the stainless steel powder and glass powder of a particle size less than about 200 microns and an acidic polymeric binder consisting of one or more curable organic polymeric materials, whereby a dental filling material is obtained.

2. The method of claim 1 further comprising the steps of filtering the acid treated stainless steel powder to separate the stainless steel powder from the acid, and washing the filtered stainless steel powder.

3. The method of claim 1 wherein the acid used to treat the stainless steel powder is selected from the group consisting of hydrochloric acid, sulfuric acid, acetic acid, propionic acid, phosphoric acid, hydrofluoric acid, perchloric acid, and nitric acid.

4. The method of claim 1 wherein the stainless steel is treated with the acid in step a) for a period of time sufficient to activate the surface of the stainless steel toward increased bonding with the polymeric binder.

5. The method of claim 2, wherein the stainless steel is washed with water.

6. The method of claim 2 wherein the stainless steel is washed with anhydrous alcohol.

7. The method of claim 6 wherein the anhydrous alcohol is methanol.

8. A dental filling material comprising: an acidic polymeric binder, glass filler, stainless steel powder filler, and one or more additives selected from the group consisting of cure enhancers, pigments, synthetic enamel, organic acids, inorganic acids, amines, adhesion promoters, oxidation inhibitors, photocurable resins, photoinitiators, camphoroquinone, diketones, benzoyl peroxide, ethanolamine, triethanolamine, tannic acid, ferric chloride, acrylamide, acrylonitrile, vinyl chloride, allyl chloride, vinyl acetate, 2-hydroxyethyl methacrylate, sodium tripolyphosphate, mineralizing agents, dodicin, calcium hydroxyapatite, gold alloys, silver alloys, precious metals, non-precious metals, porcelain materials, and materials for coating the stainless steel powder filler.

9. A dental filling material comprising an organic polymeric binder, glass filler, and stainless steel powder filler, wherein the stainless steel powder filler is surface treated.

10. The dental filling material of claim 9 wherein the surface treatment is chemical or thermal treatment of the stainless steel powder whereby the bonding of the stainless steel to the polymeric binder is increased relative to the bonding achieved in the absence of said surface treatment.

11. A dental filling material comprising an organic polymeric binder, glass filler, and stainless steel powder filler, wherein the stainless steel powder filler comprises base metal particles which have been stainless steel coated.

12. A dental filling material comprising an organic polymeric binder, glass filler, and stainless steel powder filler, wherein the stainless steel powder filler comprises base metal particles which have been chromium plated.

13. A dental filling material comprising an organic polymeric binder, glass filler, and stainless steel powder filler, further comprising one or more additives selected from the group consisting of precious metals, non-precious metals, and porcelain materials wherein the stainless steel is sintered with the additive.

14. A dental filing material comprising an organic polymeric binder, glass filler, and stainless steel powder filler, wherein the stainless steel powder filler is mixed with a precious metal.

15. A dental filling material comprising an organic polymeric binder, glass filler, and stainless steel powder filler, wherein the stainless steel powder filler is mixed with a non-precious metal.

16. A dental filling material comprising an organic polymeric binder, glass filler, and stainless steel powder filler, wherein the stainless steel powder filler is sintered with glass ionomer powder, or combined with a sintered or non-sintered mixture of sintered and non-sintered glass ionomer powder and stainless steel powder filler.

* * * * *

UNITED STATES PATENT AND TRADEMARK OFFICE
CERTIFICATE OF CORRECTION

PATENT NO. : 5,084,491
DATED : Jan. 28, 1992
INVENTOR(S) : Ronald E. Kerby

It is certified that error appears in the above-identified patent and that said Letters Patent is hereby corrected as shown below:

Title page, item 73, "The Ohio University" should be --The Ohio State University--.

Signed and Sealed this

Fifteenth Day of June, 1993

Attest:

MICHAEL K. KIRK

Attesting Officer

Acting Commissioner of Patents and Trademarks